(12) United States Patent
Bakker-Van Der Kamp et al.

(10) Patent No.: US 12,023,426 B2
(45) Date of Patent: Jul. 2, 2024

(54) BREAST SHIELD ARRANGEMENT FOR A BREAST PUMP

(71) Applicant: KONINKLIJKE PHILIPS N.V., Eindhoven (NL)

(72) Inventors: Gertrude Riëtte Bakker-Van Der Kamp, Den Helder (NL); Aafje Gijsbertha Koster, Eindhoven (NL); Johannes Tseard Van Der Kooi, Munein (NL); Daan Hendrik Gosenshuis, Waalre (NL); Christoph Dobrusskin, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 913 days.

(21) Appl. No.: 16/978,805

(22) PCT Filed: Mar. 4, 2019

(86) PCT No.: PCT/EP2019/055233
§ 371 (c)(1),
(2) Date: Sep. 8, 2020

(87) PCT Pub. No.: WO2019/174941
PCT Pub. Date: Sep. 19, 2019

(65) Prior Publication Data
US 2021/0046227 A1 Feb. 18, 2021

(30) Foreign Application Priority Data
Mar. 12, 2018 (EP) ..................................... 18161320

(51) Int. Cl.
A61M 1/06 (2006.01)
B33Y 80/00 (2015.01)

(52) U.S. Cl.
CPC ............ *A61M 1/066* (2014.02); *A61M 1/062* (2014.02); *A61M 1/064* (2014.02); *B33Y 80/00* (2014.12)

(58) Field of Classification Search
CPC ................................ A61M 1/066; A61J 13/00
See application file for complete search history.

(56) References Cited

U.S. PATENT DOCUMENTS

| 6,383,163 B1 | 5/2002 | Kelly |
| 6,461,324 B1 | 10/2002 | Schlensog |

(Continued)

FOREIGN PATENT DOCUMENTS

| FR | 1067421 | 6/1954 |
| JP | 2007089904 | 4/2007 |

(Continued)

OTHER PUBLICATIONS

Translation of JP2007089904A (Year: 2007).*

(Continued)

*Primary Examiner* — Dung T Ulsh

(57) ABSTRACT

A breast shield arrangement (300) for a breast pump is provided. The breast shield arrangement comprises a breast receiving portion (300a) with a flexible collapsible funnel (301) and a rigid frame (340) which are made as a single unit by 2K manufacturing. The flexible funnel (330) has a circumferentially extending wall (301a). The breast receiving portion (300a) has a first and second end (310, 320). The flexible funnel (330) and the rigid frame (340) are connected at the first and second end (310, 320) of the breast receiving portion (300a) during a 2K manufacturing. The flexible funnel (330) is configured to collapse if a vacuum is applied to the breast receiving portion (300a).

14 Claims, 12 Drawing Sheets

(56) References Cited

U.S. PATENT DOCUMENTS

| | | |
|---|---|---|
| 6,663,587 B2 | 12/2003 | Silver |
| 7,413,557 B2 | 8/2008 | Samson |
| 8,052,635 B1 | 11/2011 | Kelly |
| 8,323,235 B2 | 12/2012 | Bryan et al. |
| 9,498,565 B2 | 11/2016 | Nowroozi |
| 9,603,982 B2 | 3/2017 | Silver |
| 2012/0004604 A1 | 1/2012 | Van Der Kamp |
| 2014/0031744 A1* | 1/2014 | Chen .................. A61M 1/066 604/74 |
| 2015/0217034 A1* | 8/2015 | Pollen ................ A61M 1/064 604/74 |
| 2016/0015876 A1 | 1/2016 | Tattersfield |
| 2018/0078687 A1* | 3/2018 | Alvarez ............... A61M 1/06 |

FOREIGN PATENT DOCUMENTS

| | | |
|---|---|---|
| WO | 00/33897 | 6/2000 |
| WO | 2011/007140 | 1/2011 |
| WO | 2018/041365 | 3/2018 |

OTHER PUBLICATIONS

International Search Report and Written Opinion dated May 23, 2019 for International Application No. PCT/EP2019/055233 filed Mar. 4, 2019.

\* cited by examiner

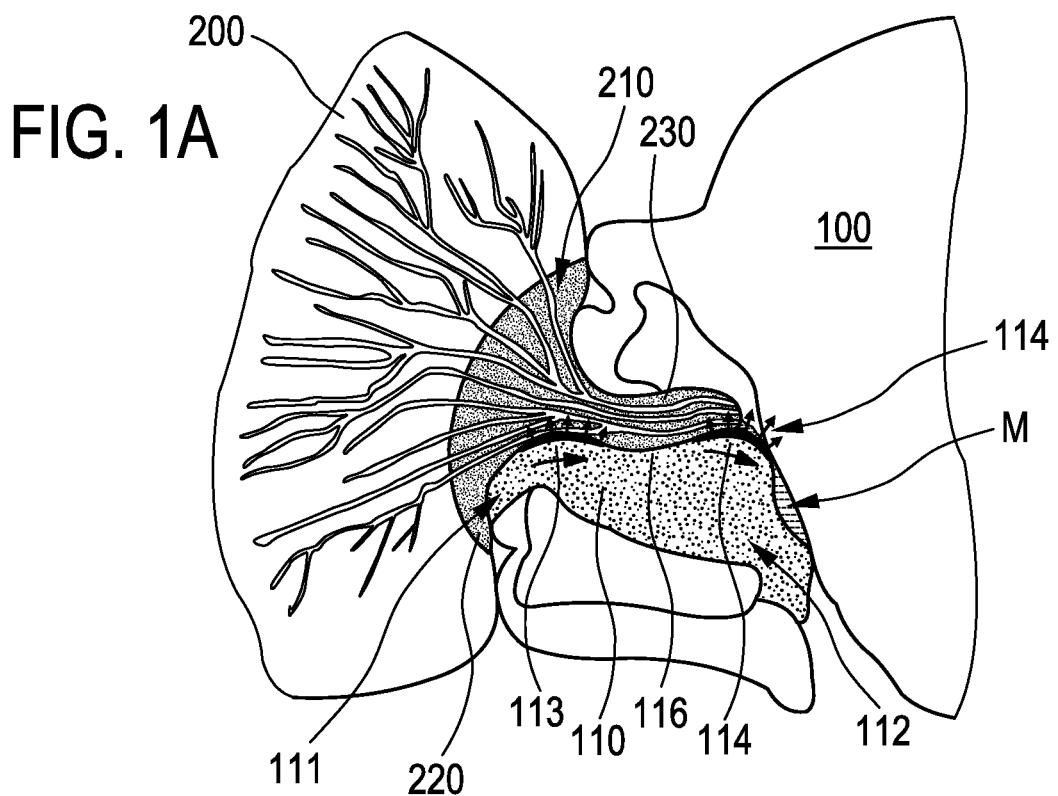
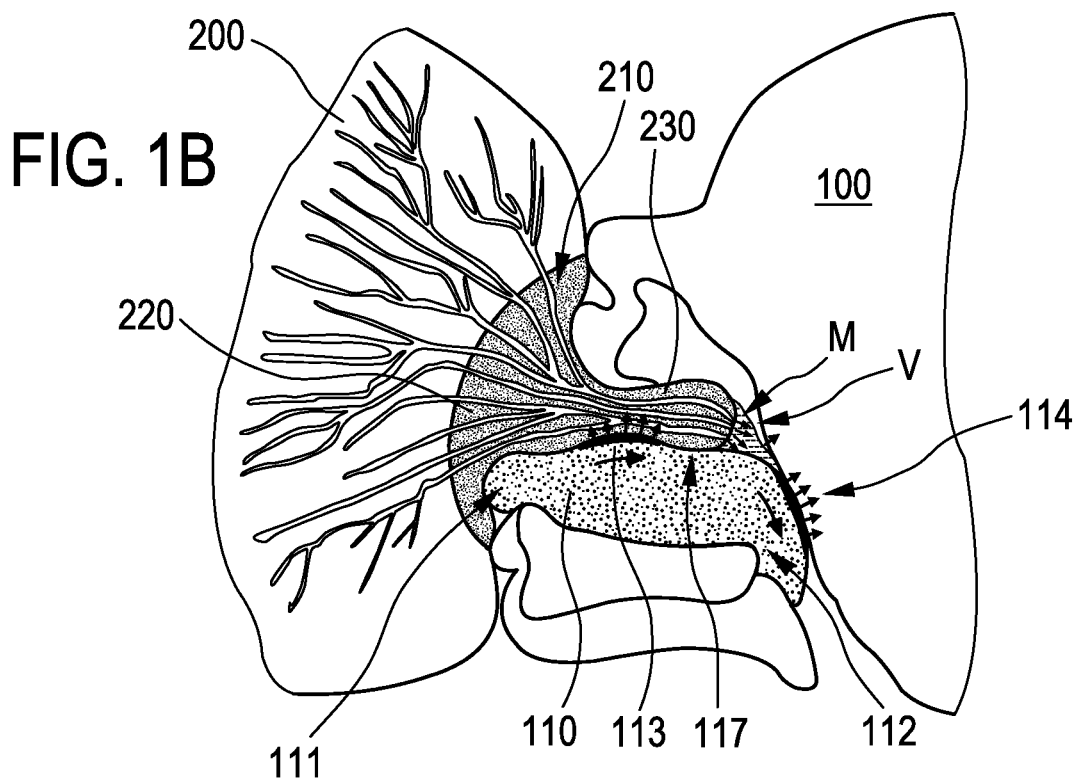

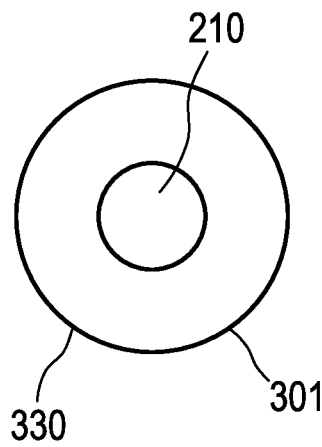 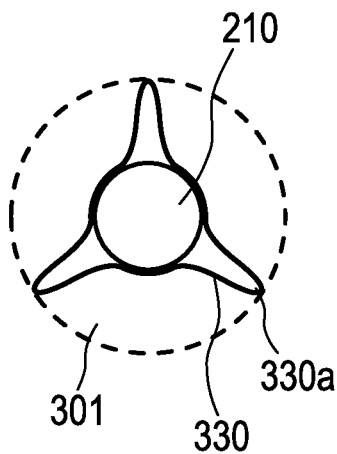 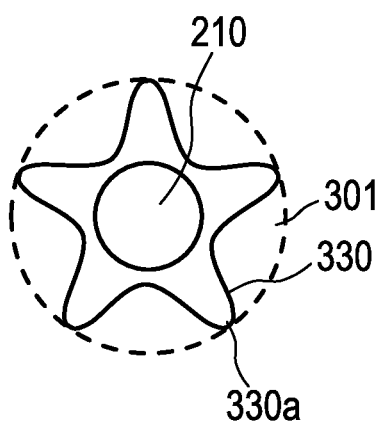
FIG. 6A  FIG. 6B  FIG. 6C
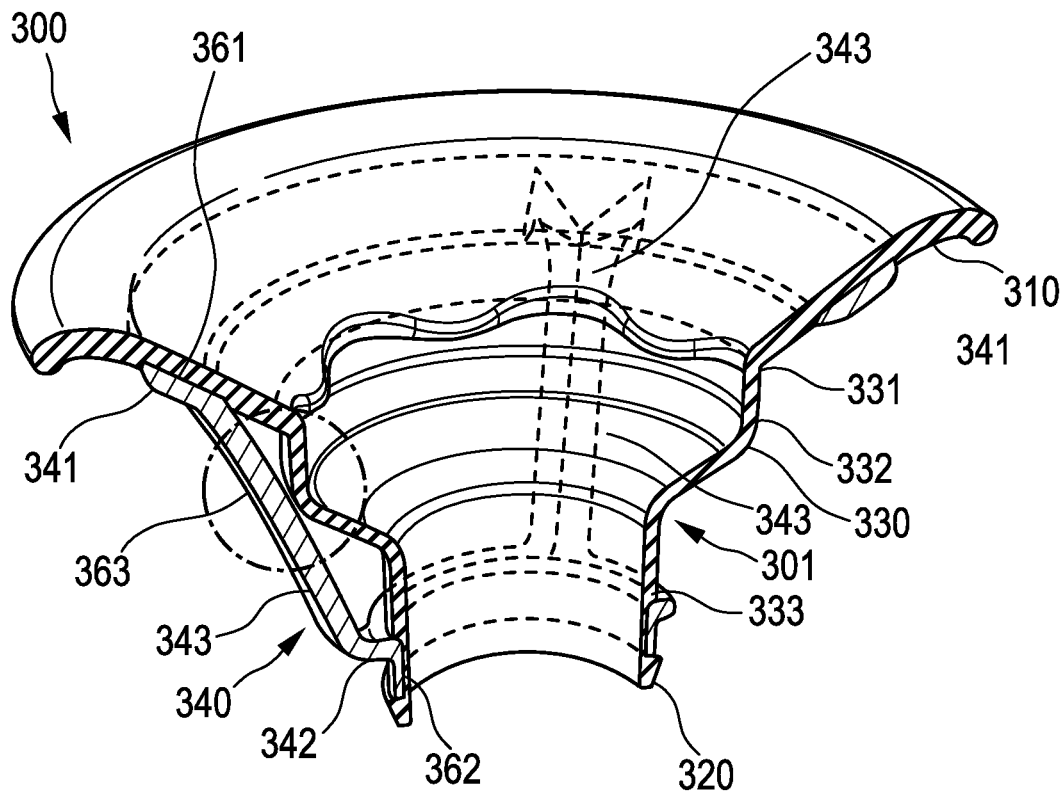
FIG. 7

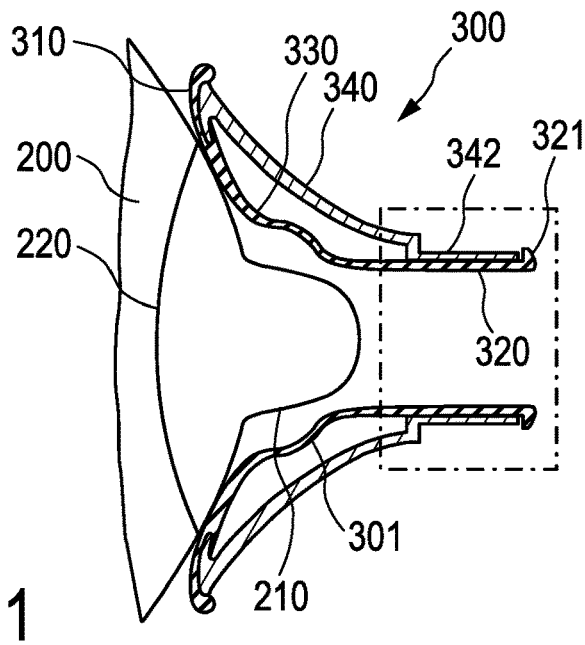
FIG. 11
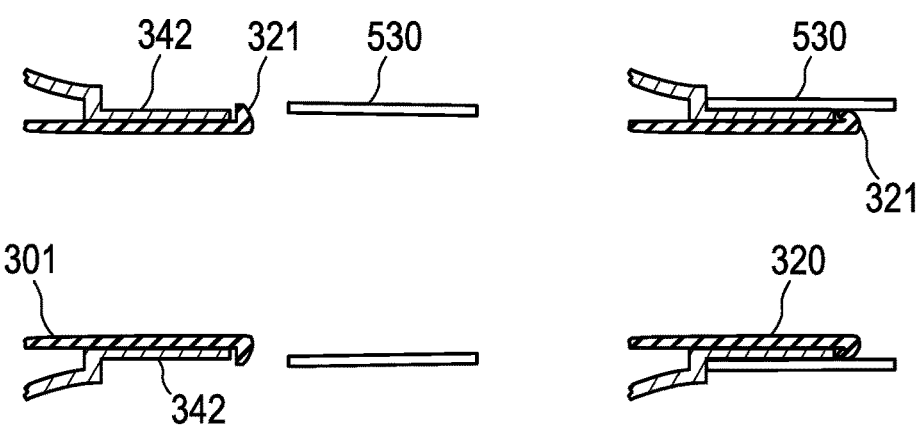
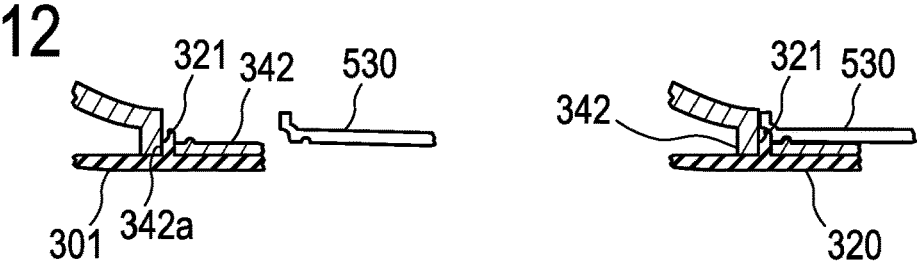
FIG. 12
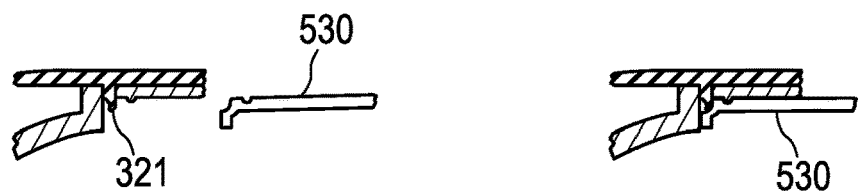

BREAST SHIELD ARRANGEMENT FOR A BREAST PUMP

CROSS REFERENCE TO RELATED APPLICATIONS

This application is the U.S. National Phase application under 35 U.S.C. § 371 of International Application No. PCT/EP2019/055233 filed Mar. 4, 2019, which claims the benefit of European Patent Application Number 18161320.9 filed Mar. 12, 2018. These applications are hereby incorporated by reference herein.

FIELD OF THE INVENTION

The invention relates to a breast shield arrangement for a breast pump as well as a breast pump.

BACKGROUND OF THE INVENTION

Breast feeding is the natural way for feeding a baby. The WHO recommends exclusively breast feeding an infant for six months and then continuing breast feeding for at least up to the age of two years. If a mother is, however, not able to feed her infant directly, e.g. because of medical problems or because of absence, the use of a breast pump allows to extract milk and to feed the breast milk to the infant through other means like a bottle.

During breast feeding, an infant or baby performs a peristaltic tongue movement. At the same time, the infant will suck on the breast of the mother. By sucking on the breast of the mother, a negative pressure is created enabling the baby to form a teat from the breast nipple, the areola and the underlying breast tissue. The baby is able to hold a base vacuum in maintaining the teat in the mouth of the baby. In addition to the base vacuum, an alternating pressure is applied with the jaw and the tongue.

FIGS. 1A and 1B show schematically and exemplary a general anatomy of the sucking of an infant. In the FIGS. 1A and 1B, an infant or baby 100 with a tongue 110 having an anterior portion 111 and a posterior portion 112 is depicted. Furthermore, a breast 200 of the breast feeding woman including milk ducts 210, an areola 220 and a nipple 230 are depicted. The infant or baby 100 is able to maintain a base vacuum in the mouth such that the nipple 230 stays in the mouth. Furthermore, the baby 100 performs peristaltic tongue movements in order to extract milk from the breast of the breast feeding woman. The baby is also able to generate a wave with its tongue. As can be seen in FIG. 1A, the tongue 110 creates a hill or bump 113 (at its anterior portion) as well as a further hill or bump 114 (at its posterior portion 112). In between these two bumps 113, 114, a valley 116 is present. As can be seen in FIG. 1B, the bump or hill 113, 114 move along the tongue of the infant. The same applies to the valley 116, 117. The milk from the milk ducts 110 are thus transported in the valleys 116, 117 through the nipples 230 into the mouth of the infant. The presence of the hills 113, 114 enables the pushing of the milk towards the mouth of the infant. At the tip of the nipple, the presence of a valley 116, 117 increases in volume which is responsible for the vacuum creation at the tip of the nipple. At the same moment, the hills 113, 114 are pushing the milk towards the exit such that the infant 110 can drink the exited milk M. The movement of the tongue creating the hills and valleys is important to stimulate a hormone production responsible for the milk ejection reflex and keeping the milk flowing.

Breast shields are known which have a funnel made of a flexible material such that it collapses when a vacuum is applied to the breast shield arrangement. The flexible funnel can typically be inserted into a rigid frame in order to hold the flexible funnel. However, problems can arise when the flexible funnel and the rigid frame are mounted. In particular, if the flexible funnel is not mounted correctly into the frame, tensions and stresses may occur in the funnel which can have a negative influence on the performance of the breast pump.

US 2016/0015876 A1 discloses a breast interface for a breast pump. The breast interface comprises a liner as well as a liner support frame. The liner is collapsible. The liner and the support frame can be manufactured as a single structural component by co-molding.

WO 2018/041365 discloses a breast shield arrangement having a funnel into which the breast is placed. The funnel comprises two ports for applying separate vacuums to the breast shield arrangement. One vacuum port is arranged at the open end of the funnel and the second port is arranged outside the funnel.

SUMMARY OF THE INVENTION

It is therefore an object of the invention to provide an improved breast shield arrangement which allows a more comfortable use of a breast shield arrangement.

According to an aspect of the invention, a breast shield arrangement for a breast pump is provided. The breast shield arrangement comprises a breast receiving portion having a flexible collapsible funnel and a rigid frame which are both made by 2K (two component) manufacturing. The flexible funnel has a circumferentially extending wall. The breast receiving portion has a first and second end. The flexible funnel and the rigid frame are connected at the first and second end of the breast receiving portion during the 2K (two component) manufacturing. The flexible funnel is configured to collapse if a vacuum is applied via the second end of the breast receiving portion. The flexible funnel comprises an at least partially circumferentially extending concave portion as seen from the first end of the breast receiving portion. The concave portion is coupled to the first end of the breast receiving portion. The vacuum applied at the second end of the breast receiving portion is the only vacuum in the breast shield arrangement.

The producing of the flexible collapsible funnel and the rigid frame by means of a 2K (two component) manufacturing is advantageous as the result is only one unit which does not need to be assembled anymore. Furthermore, as the funnel and the frame are now a single unit, there are no stresses between the funnel and the rigid frame. In addition, there is no need anymore to touch an inside surface of a funnel during assembly of the funnel and the frame which greatly improves the comfort, the ease of use and hygiene when cleaning the breast shield arrangement. Moreover, as the funnel and the rigid frame are now one piece, they cannot be disconnected during the application of vacuum to the breast shield arrangement. Moreover, because of the flexible funnel, the breast shield arrangement is adaptable to a great number of nipple and areola sizes.

According to an aspect of the invention, the flexible funnel comprises a convex portion which forms in the collapsed state of the funnel a sealing portion configured to seal a part of the nipple and/or areola against a vacuum in the breast receiving portion.

According to a further aspect of the invention, the flexible funnel has in a collapsed state at least two lobes, preferably three lobes.

According to a further aspect of the invention, the rigid frame comprises a first and second end as well as at least one leg between the first and second end. The flexible funnel and the at least two legs are at least partially connected during the 2K (two component) manufacturing at at least a first and second position. Hence, the flexible funnel is coupled to the legs of the rigid frame thus holding the flexible funnel at the at least first and second position at the two legs and thus away from the nipple of a user. Accordingly, the collapse of the flexible collapsible funnel is not incidentally but in a predetermined manner as that part of the flexible collapsible funnel which is coupled to the legs of the rigid frame will correspond to the lopes of the flexible funnel in the collapsed state. Accordingly, those areas of the nipple which are in direct contact with the collapsed funnel are not subject to the vacuum applied to the breast shield arrangement. Hence, those parts of the nipple are not undergoing the same amount of stress which is in particular helpful in case of sore nipples (cracked nipples, inflammation). In addition, as the collapsible funnels are not rotational symmetric and because of the lopes which are present when the flexible funnel is in a collapsed state, the nipple will be centrally positioned within the flexible funnel when the funnel is in the collapsed state.

According to a further aspect of the invention, the flexible funnel comprises a convex portion and the at least first and second positions are arranged at the convex portion. As the flexible funnel is connected to the legs at the convex portion of the funnel, the convex portion will not come into contact with the areola and the nipple of the user in the area of the first and second position such that a first point of contact between the flexible funnel and the nipple of the user will be in a portion of the funnel between the second end and the convex portion. This is advantageous as the first point of contact between the funnel and the breast of the user is the nipple of the user which allows a more natural expression of milk as this is similar to the sucking motion of a baby.

According to a further aspect of the invention, the first end of the flexible funnel and/or the first end of the rigid frame form a first sealing portion which serves to seal the breast shield arrangement against a breast of a user.

According to a further aspect of the invention, the flexible funnel comprises a concave portion between the convex portion and the second end. The concave portion forms in the collapsed state of the funnel a second sealing portion configured to seal a part of the nipple against a vacuum in the breast receiving portion.

According to a further aspect of the invention, the breast shield arrangement comprises an expression kit having a first and second port. The first port is configured to receive the second end of the breast receiving portion. The flexible funnel comprises a third circumferentially sealing portion at the second end. The third sealing portion is configured to seal the breast receiving portion against the expression kit.

According to a further aspect of the invention, the breast shield arrangement comprises an expression kit having a first and second port wherein the first port is configured to receive the second end of the breast receiving portion. The flexible funnel comprises a third circumferentially sealing portion between the concave portion and the second end. This third sealing portion serves to seal the breast receiving portion against the expression kit.

According to an aspect of the invention, an inner diameter of the intermediate portion is continuously reduced between the first and second end of the intermediate portion.

According to a further aspect of the invention, a wall thickness of the curved portion is substantially constant.

A breast shield arrangement is provided for a breast pump. The breast shield arrangement comprises a breast receiving portion with a flexible collapsible funnel as well as a rigid frame. The funnel and the frame are made as a single unit by 2K manufacturing. The flexible funnel has a circumferentially extending wall and the breast receiving portion has a first and second end. The flexible funnel and the rigid frame are connected at the first and second end of the breast receiving portion at at least a first and second position during the 2K manufacturing. The flexible funnel is configured to collapse if a vacuum is applied to the breast receiving portion. The rigid frame comprises a first and second end as well as at least one leg between the first and second end. The flexible funnel and the at least one leg are at least partly connected during the 2K manufacturing at at least a third position.

According to an aspect of the invention, a breast pump is provided with a breast shield arrangement as described above.

The 2K (two component) manufacturing according to an aspect of the invention can correspond to a 2K injection moulding, a 3K (three component) injection moulding, 3D printing as well as rapid prototyping. Furthermore, during the 2K manufacturing, it is also possible that parts of the funnel and the rigid frame are glued together. Accordingly, 2K manufacturing relates to a manufacturing with at least two components (2K) which typically have different material characteristics. During the 2K manufacturing, a piece is manufactured which can be made of two different components. In other words, during the 2K manufacturing, at least two components with different material characteristics are combined into a single piece.

The breast shield arrangement according to the aspects of the invention are more comfortable to use as the area of the nipple which is exposed to the vacuum is reduced which leads to also a reduced tissue stretching. Moreover, as the actual area which is exposed to vacuum of the nipple can be reduced, the vacuum level can be increased without compromising the comfort for the user. Moreover, sore and cracked nipples can be supported by the collapsed funnel and are thus not exposed to vacuum.

Furthermore, due to the non-rotational collapse of the flexible funnel, an increased tissue support at cracked or sore nipples is possible by rotating the breast shield. Furthermore, the breast shield according to the aspects of the invention enable a more specific emptying of buts which may be clogged or which may be inflamed.

According to an embodiment of the invention, when no vacuum is applied to the breast shield arrangement via its second end, the flexible funnel is configured such that a nipple of the user can be inserted without coming into contact with the concave portion. Only when vacuum is applied, then the flexible funnel can collapse and can come into contact with at least a nipple of the user. It shall be understood that a preferred embodiment of the present invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

In the following drawings:

FIGS. 1A and 1B show schematically and exemplary a general anatomy of the sucking of an infant.

FIGS. 6A to 6C show a schematic cross section of a funnel according to an aspect of the invention.

FIG. 7 shows a schematic representation of a breast receiving portion according to an aspect of the invention.

FIGS. 11 and 12 each show a schematic representation of a breast shield arrangement according to an aspect of the invention.

DETAILED DESCRIPTION OF EMBODIMENTS

Figure 2:
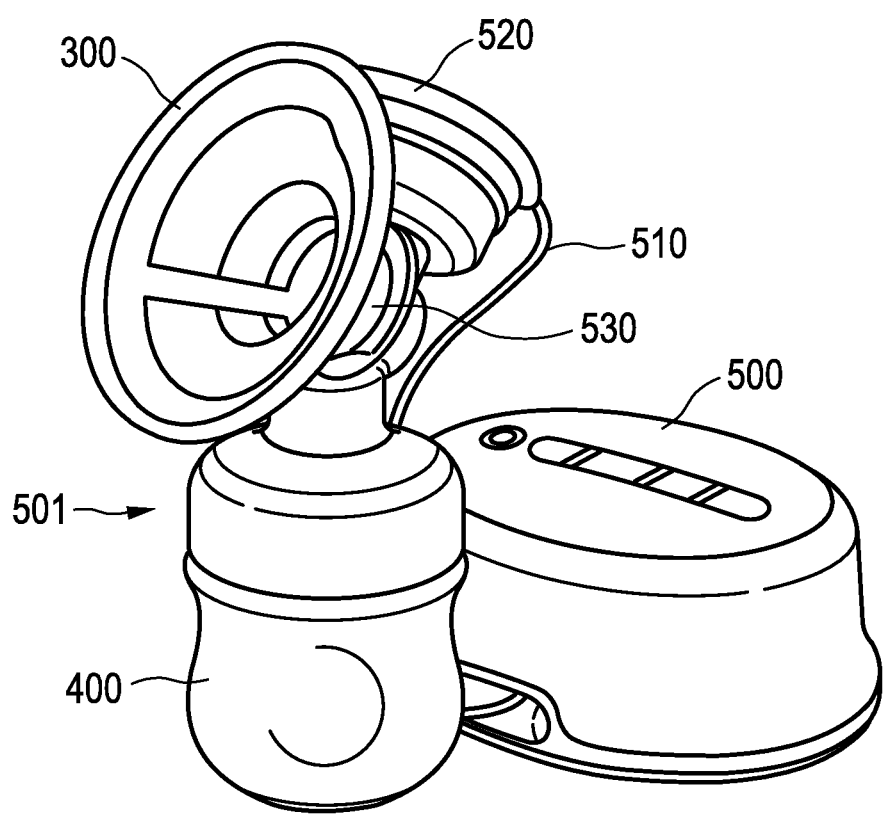
FIG. 2 shows a schematic set up of a breast pump according to an aspect of the invention.

FIG. 2 shows a schematic set up of a breast pump according to an aspect of the invention. The breast pump comprises an expression kit 501 with a funnel shaped breast shield 300, optionally a bottle 400 as well as a vacuum pump 500 and a vacuum conduit 510. When a breast of the user is placed into the breast shield 300 and the pump 500 is switched on, the pump 500 will create a vacuum in the breast shield 300 and part of the expression kit 501 via the conduit 510. Thus, the extraction of milk can be performed. The milk extracted from the breast will flow into the bottle 400. The expression kit 501 comprises a first port 530 to which one end of the breast shield 300 can be coupled such that a vacuum can be applied in the breast shield.

The vacuum applied via one end of the breast shield 300 is the only vacuum that is applied to the breast shield arrangement. Accordingly, the breast shield can collapse due to the vacuum at one end of the breast shield.

Figure 3:
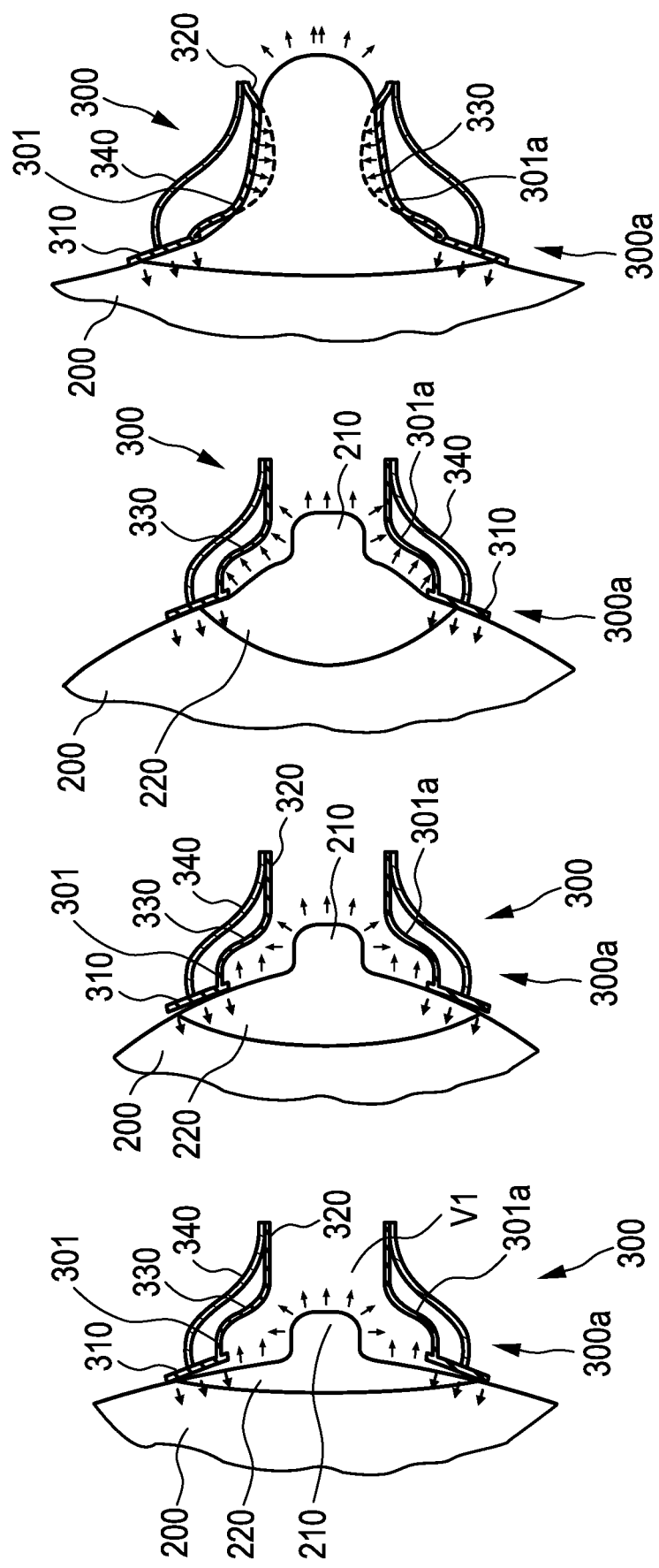
FIG. 3 shows a schematic cross section of a breast shield arrangement according to an aspect of the invention.

FIG. 3 shows a schematic cross section of a breast shield arrangement according to an aspect of the invention. In FIG. 3, a breast 200 having an areola 220 and a nipple 210 are depicted which is placed inside a volume V1 defined by a breast shield 300. The breast shield 300 may comprise a breast receiving portion or volume 300a having a support frame or structure 340 made from a hard material as well as an insert (like a funnel) 301. The insert or funnel 301 is preferably made from soft material like soft silicon (with shore 30-50, preferably 40 shore). The support structure 340 and the insert/funnel are made by a 2K injection molding process. Thus, the support structure 340 and the insert/funnel are manufactured as one single unit. The insert or funnel 301 comprises a first end 310 which acts as a (first) sealing portion 310. The insert 301 also comprises a second end 320. The second end 320 can be coupled to the first port 530 of the expression kit 501 so that vacuum can be applied to the breast shield, i.e. the funnel via the first port and the second end 320. The first end 310 of the breast shield 300 is designed to receive a breast 200 of a breast feeding woman. Through the second end 320 of the breast shield 300, the extracted milk can flow into for example a bottle 400 as shown in FIG. 2.

The insert 301 also comprises an intermediate portion 330 between the sealing portion or the first end 310 and the second end 320 of the breast shield 300. Thus, the breast 200 is shielded against the outside atmosphere so that a vacuum can be created in the volume defined by the breast 200 of a user and the surrounding intermediate portion 330. The outside of the insert 301 is subject to the atmospheric pressure. Accordingly, the flexible insert 301 will collapse because of the vacuum as applied at one end of the flexible insert 301.

In FIG. 3, the different steps are depicted when the breast shield 300 is placed against a breast of a user such that the breast 200 is placed into a volume V1 and the vacuum is applied. First of all, the (first) sealing portion 310 will be placed against the areola 220 of the user. Then when vacuum is applied, the collapsible intermediate portion 330 will collapse and come into contact with the nipple 210 of the user before the intermediate portion 330 is in contact with the areola 220 of the user. With the breast shield arrangement according to the invention, it is possible to simulate a natural pumping which corresponds to the sucking of a baby. This is achieved by stimulating the milk let-down by firstly bringing the nipple 210 into contact with the intermediate portion 330 before the areola 220 is touched by the intermediate portion 330. It should be noted that of course the sealing portion 310 must first come in contact with the areola and the breast of the user such that a vacuum can be generated. However, the collapsible intermediate portion 330 comes first into contact with the nipple 210 and only thereafter with the areola 220. This is advantageous as the nipple is compressed and supported while forming a teat avoiding overstretching or rubbing. The breast shield according to the invention is advantageous as it fits substantially every nipple size.

The intermediate portion 330 is designed to collapse when a vacuum is applied. In this case, the intermediate portion 330 will adhere to or surround the nipple 210 of the user.

Preferably, the support frame or structure 340 is implemented as a hard plastic body part which should be stiff and can provide support for the insert 301. The insert 301 and the support structure 340 are made by a 2K (two component) injection molding. The sealing portion 310 of the insert 301 together with the first end 341 of the support structure 340 can implement a sealing function to enable a vacuum in the volume defined by the nipple of the user and the intermediate portion 330. Preferably, the sealing portion 310 of the insert is placed at least partly against the areola 220 of the user such that the nipple 210 is typically not in contact with the sealing portion 310 when the breast shield 300 is placed over the breast 200 of a user. In particular, the intermediate portion 330 is implemented such that when it is collapsing due to an applied vacuum, the collapsing intermediate portion will first touch the nipple before it touches the areola. Furthermore, preferably the intermediate portion 330 is implemented such that the surface of the nipple is supported during a vacuum cycle. Preferably, the insert is made of soft silicon and is flexible such that it allows a collapsing behavior.

When a vacuum is applied to the breast shield by means of the vacuum pump 500 and when the pressure inside a volume defined by the breast and the breast shield (namely the intermediate portion 330) is sufficiently smaller than the atmosphere outside the intermediate portion 330 (e.g. the atmosphere pressure) the intermediate portion 330 will collapse and come into contact with the areola 220 and the nipple 210.

Figure 4:
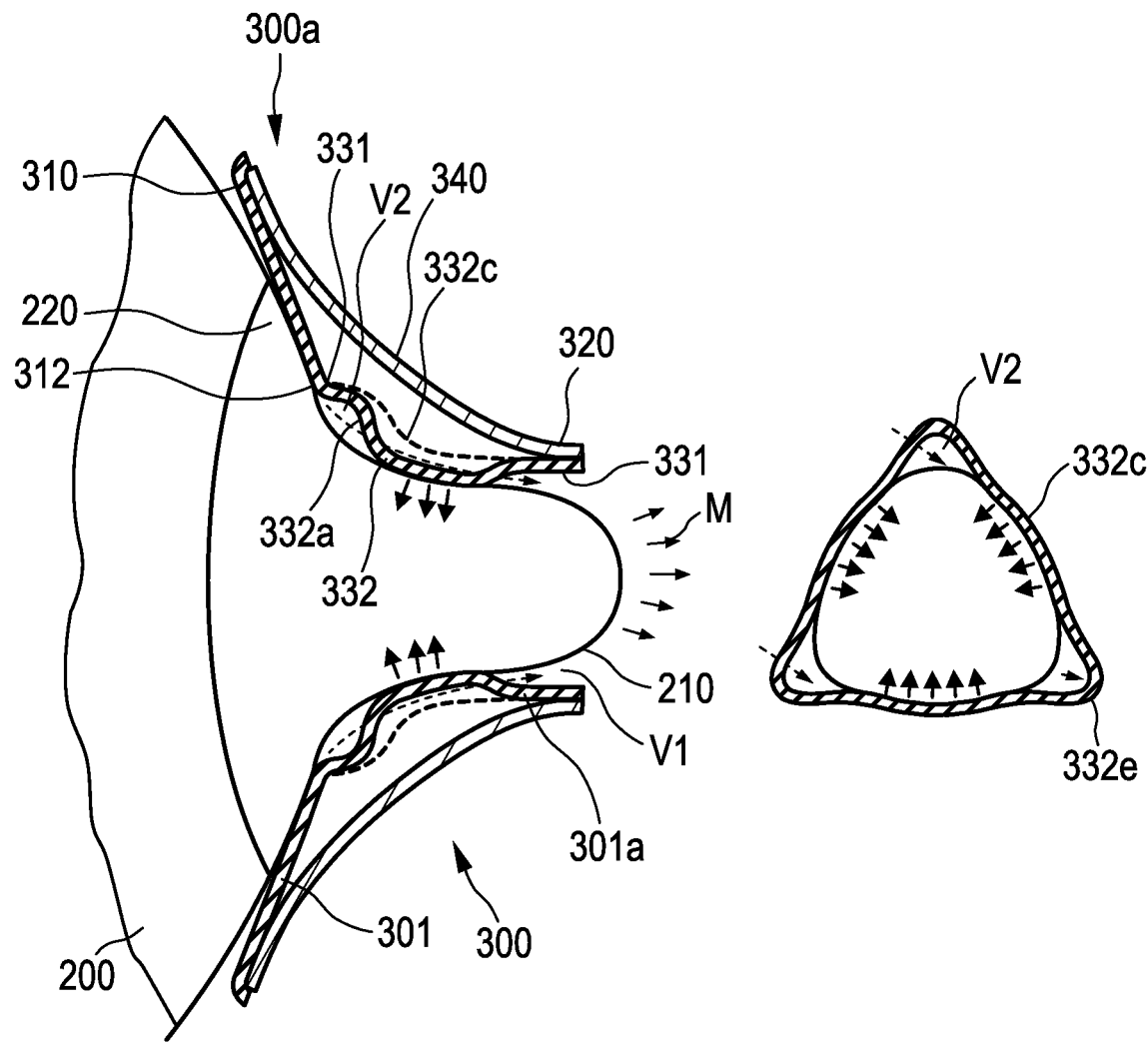
FIG. 4 shows a schematic cross section of a breast shield arrangement according to an aspect of the invention.

FIG. 4 shows a schematic cross section of a breast shield arrangement according to a further aspect of the invention. In FIG. 4, an intermediate step during the creation of the vacuum is depicted. A breast 200 is placed into a first volume V1 defined by the breast shield 300 (in particular the funnel 301). The funnel 301 comprises a first sealing portion 310 which serves to seal the breast receiving portion against a breast 200 of a user. Adjacent to the sealing portion 310, a concave portion 332a is provided which is preferably circumferentially extending. Between the concave portion 332a and the second end 320 of the funnel 301, a convex portion 332c is provided. Here, a curved portion 332 of the intermediate portion 330 and in particular a second curved section (a convex portion) 332c is in contact with the nipple 310 of the user. While the second curved section 332c is in contact with the nipple 310, the section 332e (in form of a lobe) is not in contact such that a second volume V2 is created between the first sealing portion 310 and a second sealing portion 332c defined by the point of contact between the nipple 210 and the curved section 332c. The intermediate portion 330 forms substantially a triangle as shown in FIG. 4. By means of these portions 332e, a vacuum connection is still present towards the areola 220 of the user.

Figure 5C:
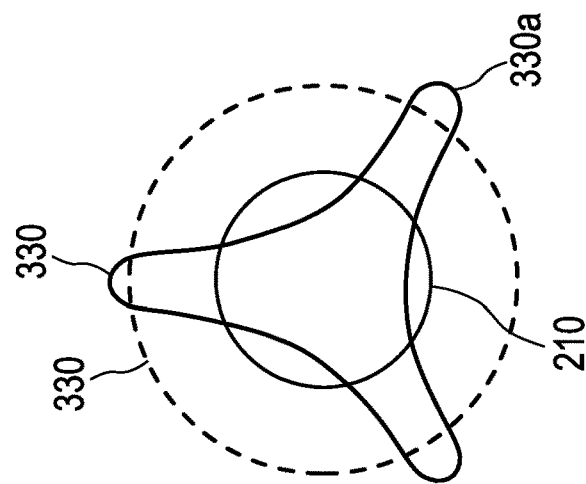
FIGS. 5A to 5C show schematic views of a collapsible intermediate portion according to an aspect of the invention.
Figure 5B:
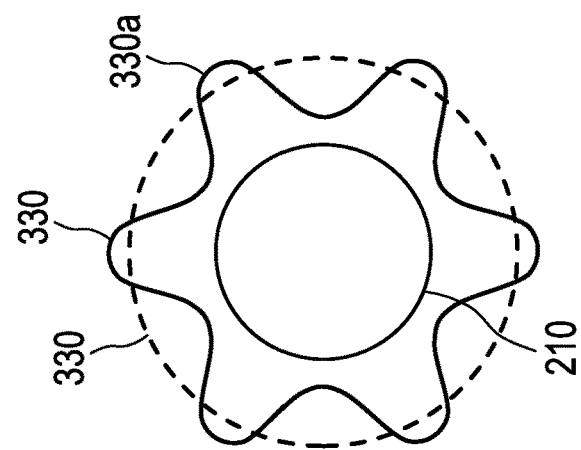
Figure 5A:
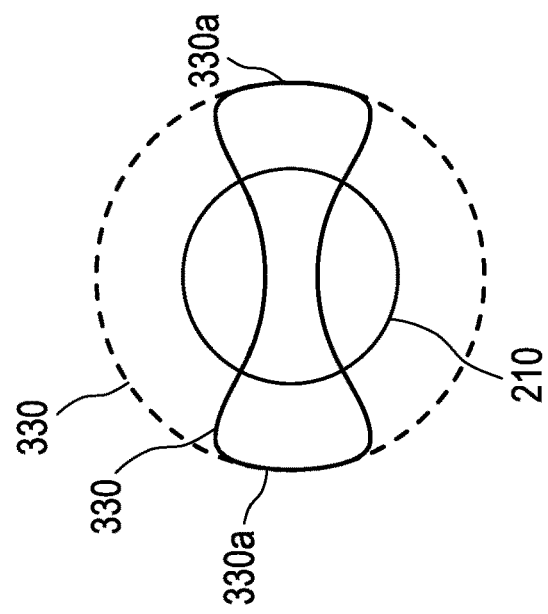

FIGS. 5A to 5C show schematic views of a collapsible intermediate portion according to an aspect of the invention. The FIGS. 5A 5C are used to illustrate a side view of the intermediate portion 330. When the collapsible portion has collapsed, the intermediate portion 330 will have two lopes 330a. In the FIGS. 5A 5C, the intermediate portion 330 is shown in an uncollapsed state (broken lines) and in a collapsed state (solid lines). FIG. 5B shows an intermediate portion 330 which comprises, when collapsed, a plurality of lopes 330a. In FIG. 5C, an intermediate portion 330 is depicted which when collapsed comprises three lopes 330a. Due to the dimensions of the intermediate portion 330 (in particular due to the reduced length of the intermediate portion 330), the intermediate portion 330 comprises several lopes when the intermediate portion is in a collapsed state. In order to in-crease the surface of the nipple 210 of the user which is in direct contact with the intermediate portion 330 when it has collapsed, it is advantageous if the number of lopes is reduced (as compared between FIG. 5B and FIG. 5C).

FIGS. 6A 6C show a schematic cross section of a funnel according to an aspect of the invention. In FIG. 6A, the funnel 301, 330 is shown when no vacuum is applied. The nipple 210 is placed into the funnel 301, 330. In FIG. 6B, the situation with an applied vacuum is depicted. In particular, the funnel 301, 330 has collapsed and comprises three lopes 330a. FIG. 6C shows a situation where the funnel 301, 330 has collapsed and comprises five lopes.

FIG. 7 shows a schematic representation of a breast receiving portion according to an aspect of the invention. In FIG. 7, in particular a breast receiving portion in form of a breast shield is depicted. The breast shield is made of a support structure 340 as well as an insert in form of a flexible collapsible funnel 301, 310, 320, 330 which are both manufactured as a single unit by 2K (two component) injection molding. The funnel 301 comprises a first end 310 which serves as a first sealing portion and a second end 320 which can be placed into a port of the expression kit. Between the first and second end 310, 320, an intermediate portion 330 is provided. The insert or funnel 301 as well as the support frame 340 are manufactured by a 2K injection molding process. The support frame 340 comprises a first end 341, a second end 342 as well as at least one leg 343 which are connected between the first and second end 310, 320. The first end 341 of the support frame 340 is connected during the 2K injection molding process with a first end 310 of the insert. The second end 342 of the support frame 340 is coupled during the 2K injection molding process to a second end 320 of the flexible funnel. Furthermore, the intermediate portion 330 can comprise a curved portion 332. This curved portion 332 can be curved outwardly (and forms a concave portion). The curved portion 332 (and in particular the concave portion) is coupled to one of the legs 343 during the 2K injection molding. In other words, the insert 301 is coupled to the support frame at three points, namely at a first point 361 (connecting the first end 341 of the support frame and the first end 310 of the insert). A second point of contact 362 is provided at the second end 320 of the insert as well as the second end 342 of the support frame. A third point of contact 363 is provided between the leg 343 and the curved portion 332 (in particular the concave portion). The third point of contact 363 can be arranged at the middle halfway between the first and second end. This third point of contact 363 is advantageous as it enables to control the number of lobes and also to predict at which position the lobes will collapse. It should be noted that the positions of the third point of contact 363 and the knowledge of the position of the third point of contact 363 can be used may users of the funnel to avoid extra stress on cracked or sore nipple tissue. Furthermore, this can also be used to empty milk ducts which can be clogged. In particular, with the knowledge of the third point of contact, the user can position the lobes on those areas with cracked and sore tissues or to enable the emptying clogged milk ducts. In particular, with the breast shield arrangement according to an aspect of the invention, sore nipples and breast inflammation can be significantly prevented or reduced.

Figure 8:
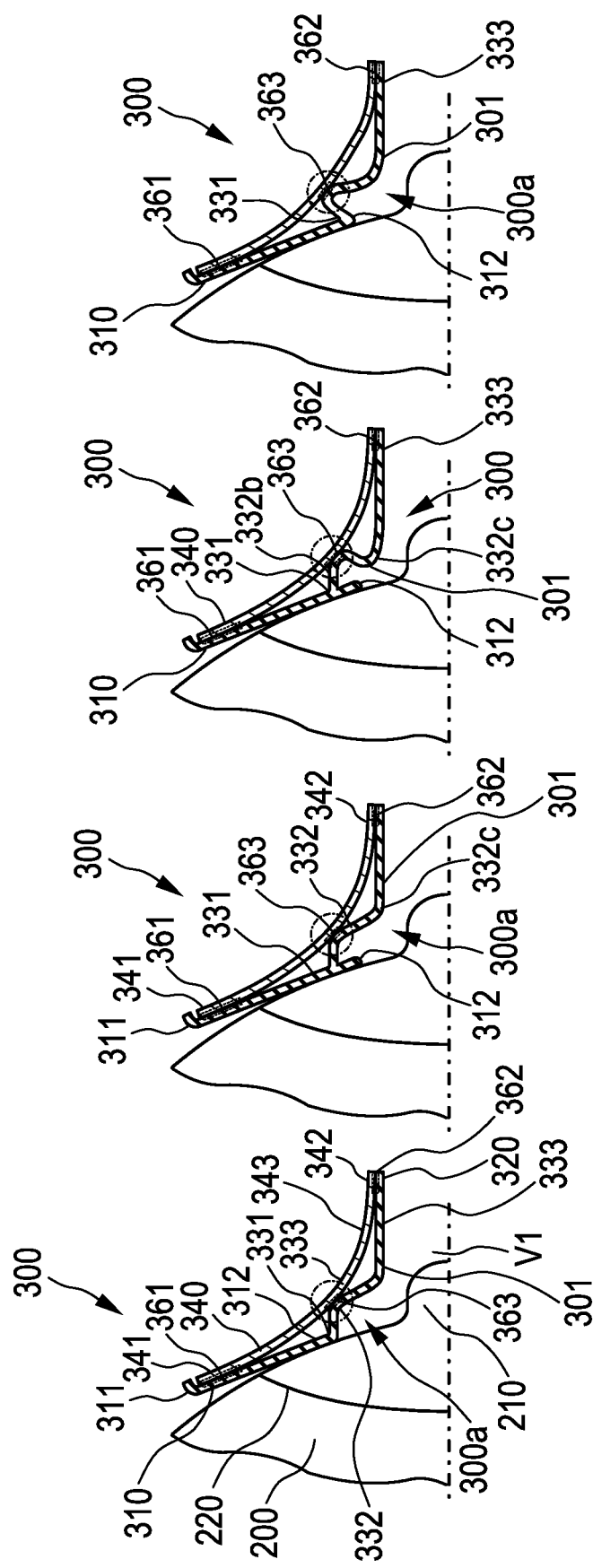
FIG. 8 shows a schematic cross section of a breast shield arrangement according to an aspect of the invention.

FIG. 8 shows a schematic cross section of a breast shield arrangement according to an aspect of the invention. In FIG. 8, a breast 200 having an areola 220 and a nipple 210 are depicted which is placed inside a volume V1 defined by a breast shield 300. The breast shield 300 may comprise a breast receiving portion 300a having a support frame or structure 340 made from a hard material as well as a flexible insert 301, 310, 320, 330. The insert 301 is preferably made from soft material like soft silicon. The support structure 340 and the insert/funnel are made by a 2K injection molding process. Thus, the support structure 340 and the insert/funnel are manufactured as one single unit. The insert 301 comprises a first end 310 which acts as a sealing portion 310. The insert also comprises a second end 320. The first end 310 of the breast shield 300 is designed to receive a breast 200 of a breast feeding woman. Through the second end 320 or port of the breast shield 300, the extracted milk can flow into for example a bottle 400 as shown in FIG. 2. The milk flow and vacuum flow can be separated. Multiple openings may be present in the breast shield.

The insert 301 also comprises a flexible and collapsible intermediate portion 330 between the sealing portion or the first end 310 and the second end 320 of the breast shield 300.

The sealing portion 310 comprises a first end 311 and a second end 312. The second end 312 of the sealing portion 310 is placed against the areola 220 or a breast 200 of a user. Thus, the breast 200 is shielded against the outside atmosphere so that a vacuum can be created in the volume defined by the breast 200 of a user and the surrounding intermediate portion 330.

According to the invention, the support frame 340 comprises a first end 341 and a second end 342. The first end 341 can be in contact with the first end 311 of the sealing portion 310. Each of them can serve as a seal. The second end 342 is in contact with the second end 320 of the breast shield 300. Moreover, the intermediate portion 330 may be in contact with the support frame or structure 340 at other points. The intermediate portion 330 is designed to collapse when a vacuum is applied. In this case, the intermediate portion 330 will adhere to or surround the nipple 210 of the user.

Preferably, the support frame or structure 340 is implemented as a hard plastic body part which should be stiff and can provide support for the insert. The sealing portion 310 of the insert together with the first end 341 of the support structure 340 can implement a sealing function to enable a vacuum in the volume defined by the nipple of the user and the intermediate portion 330. Preferably, the sealing portion 310 of the insert is placed at least partly against the breast or the areola of the user such that the nipple is typically not in contact with the sealing portion 310 when the breast shield 300 is placed over the breast 200 of a user. In particular, the intermediate portion 330 is implemented such that when it is collapsing due to an applied vacuum, the collapsing intermediate portion will first touch the nipple or areola before it touches the rest of the breast. Furthermore, preferably the intermediate portion 330 is implemented such that the surface of the nipple is supported during a vacuum cycle. Preferably, the insert is made of soft silicon and is flexible such that it allows a collapsing behavior.

As shown in FIG. 8, the intermediate portion 330 has a first end 331 which is coupled with the sealing portion 310. The intermediate portion 330 furthermore comprises a second end 333 which is arranged at the second end 320 of the breast shield 300. In between the first and second end 331, 333, the curved portion 332 is present. The intermediate portion 330 comprises a first end 331, a second end 333 and a curved portion 332 in between the first and second end 331, 333. In other words, the length of the curved portion 332 is greater than a distance between the first and second ends of the intermediate portion. The curved portion 332 comprises a first end 332*a*, a second end 332*d* and optionally a first and second curved section 332*a*, 332*c* between the first and second end 332*a*, 332*d*. The first curved section corresponds to the concave portion and the second curved section corresponds to the convex portion. In the left hand picture in FIG. 8, the first end 331 of the intermediate portion 330 is coupled to the second end 332 of the sealing portion 310. In the second picture, the first end 331 of the intermediate portion 330 is coupled to the sealing portion 310 at a predetermined distance from the second end 312. In the third picture, the first end 331 is coupled to the sealing portion 310 at a predetermined distance from the second end 312 of the sealing portion 310. In the fourth picture, the second end 312 of the sealing portion 310 is coupled to a first end 331 of the intermediate portion 330.

Depending on the length of the intermediate portion 330 and in particular the curved portion 332, at least a first and second curved section 332*b*, 332*c* is present.

When a vacuum is applied to the breast shield by means of the vacuum pump 500 and when the pressure inside a volume defined by the breast and the breast shield (namely the intermediate portion 330) is sufficiently smaller than the atmosphere outside the intermediate portion 330 (e.g. the atmosphere pressure) the intermediate portion 330 will collapse and come into contact with the areola 220 and the nipple 210. In particular, the position of the lobes will also be determined by the position of the contact points 363.

Figure 9A:
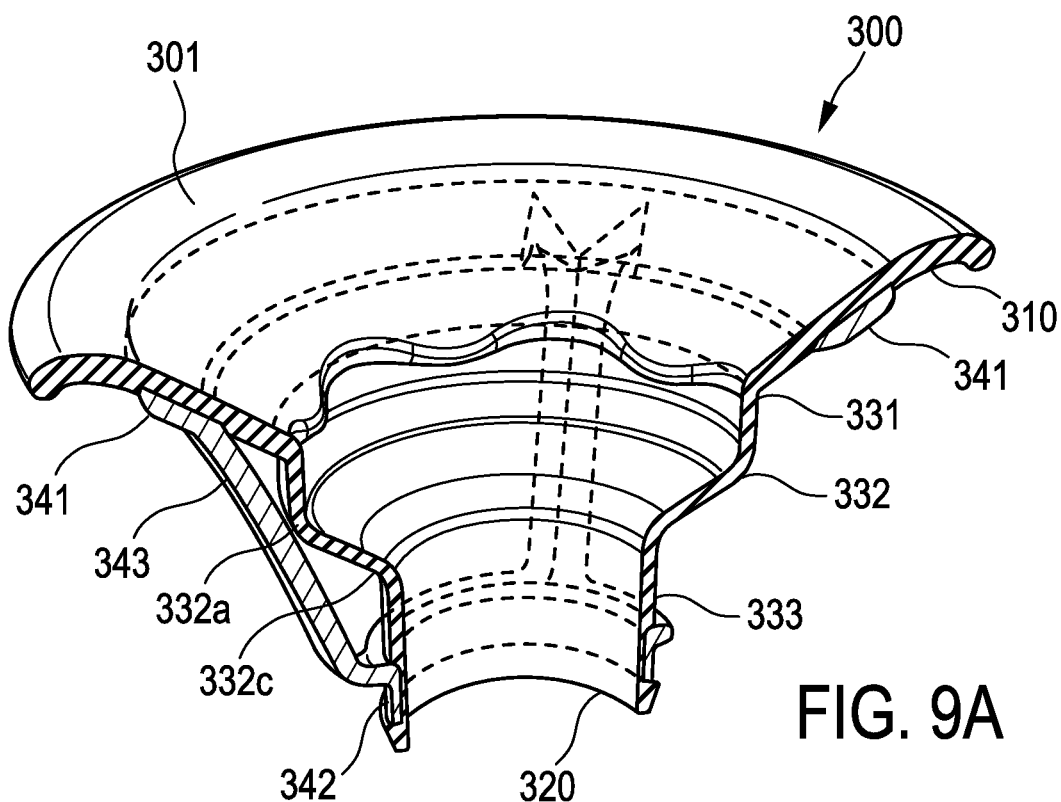
FIGS. 9A and 9B each show different schematic representations of a breast receiving unit according to an aspect of the invention.
Figure 9B:
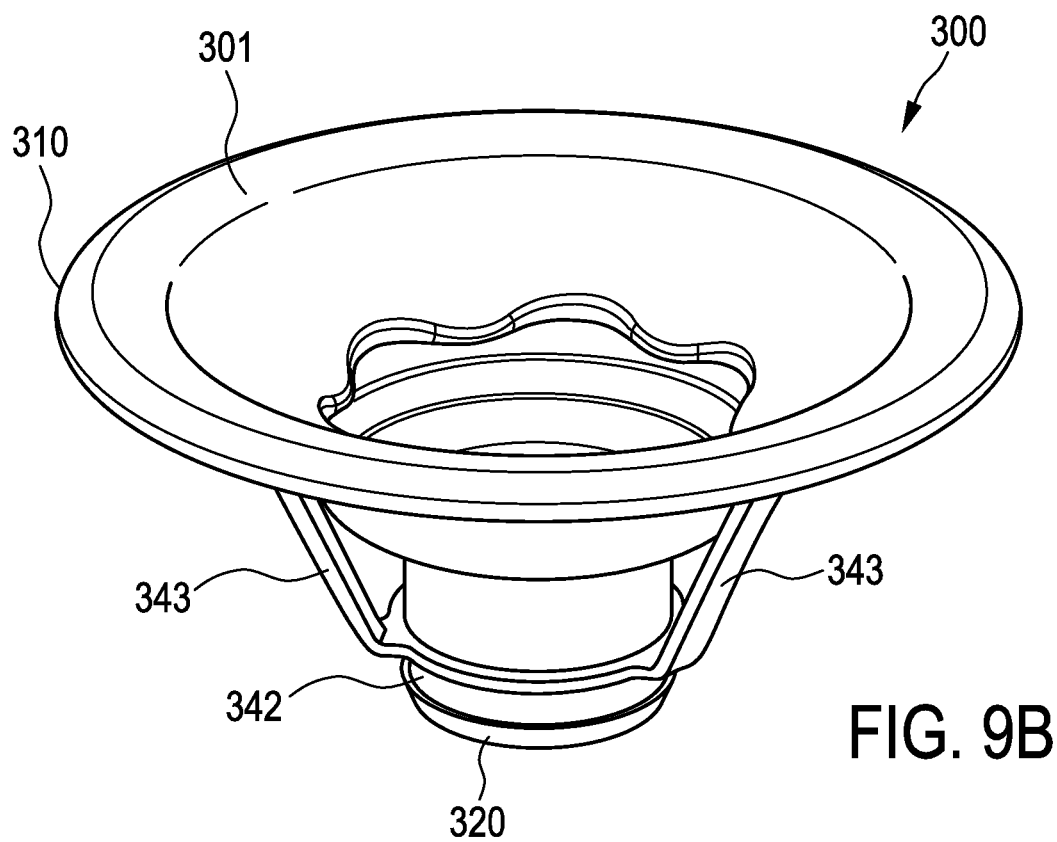

FIGS. 9A and 9B each show different schematic representations of a breast receiving unit according to an aspect of the invention. The structure of the breast receiving unit according to FIGS. 9A and 9B substantially corresponds to the structure of the breast receiving unit according to FIG. 7 with the exception that the legs 343 are not necessarily coupled to the curved portion 332 of the intermediate portion 330 during the 2K injection molding.

Figure 10B:
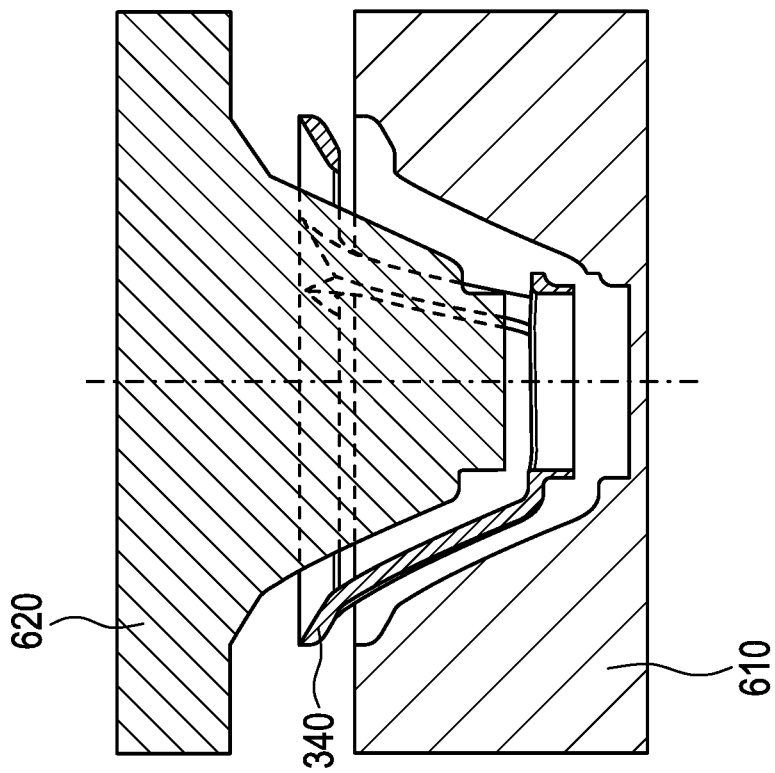
FIGS. 10A to 10D each show a schematic representation during the manufacturing of the breast receiving portion according to an aspect of the invention.
Figure 10A:
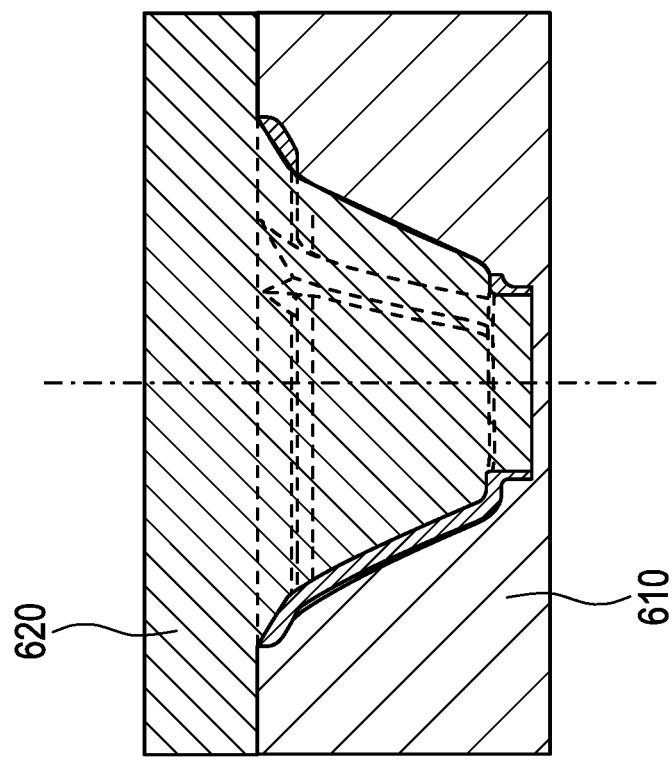
Figure 10D:
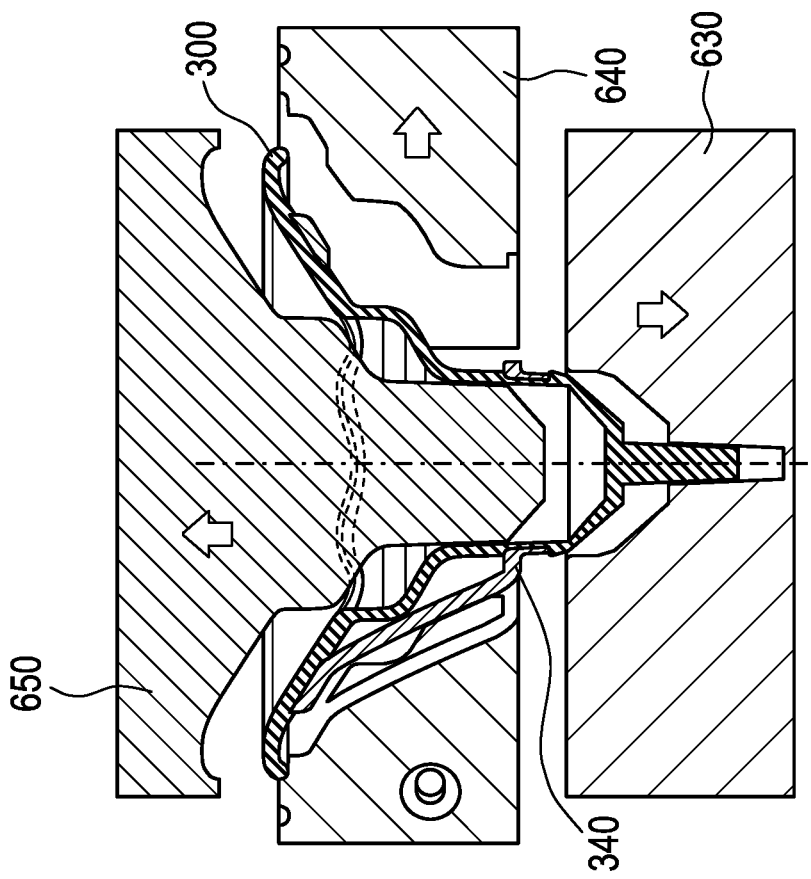
Figure 10C:
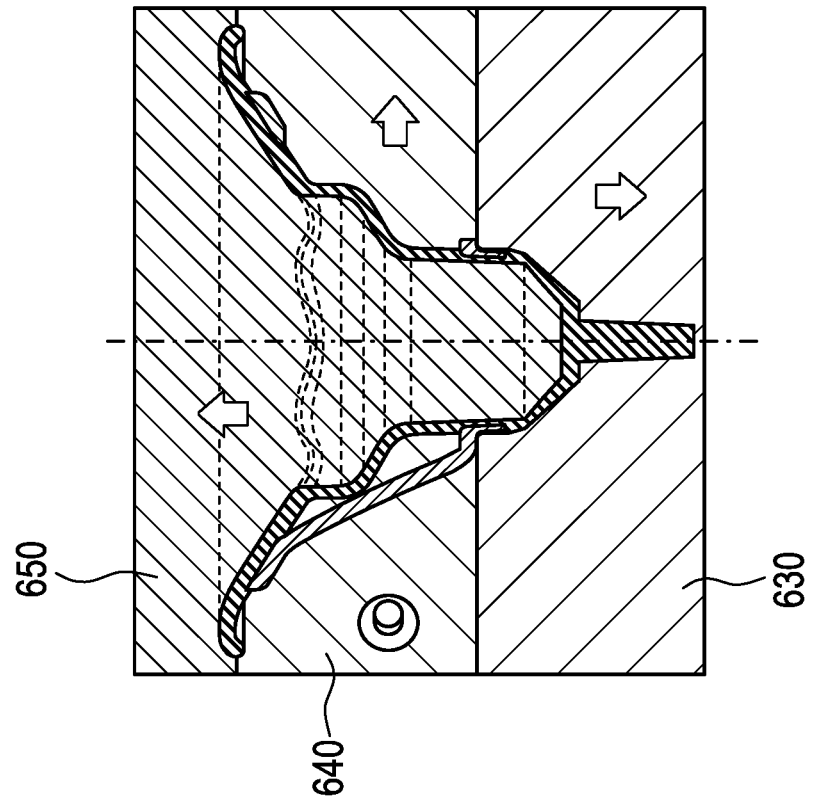

FIGS. 10A-10D each show a schematic representation during the manufacturing of the breast receiving portion. In FIGS. 10A and 10B, the manufacturing of the support frame is depicted. A bottom mold 610 and a top mold 620 are provided for the 2K injection molding. In FIG. 10B, the top mold 620 is removed together with the support frame 340. In order to manufacture the flexible funnel, three molds 630, 640, 650 are required. In particular, a bottom mold 630, a top mold 650 as well as an intermediate mold 640 are needed. Preferably, the intermediate mold 640 can be split into different parts in order to move along the legs 343 of the support frame 340.

FIGS. 11 and 12 each show a schematic representation of a breast shield arrangement according to an aspect of the invention. In FIG. 11, the flexible funnel 301 comprises a sealing 321 at its second end 320 such that the funnel 301 can be sealed against a port 530 of the expression kit 501 by means of the seal 321. The breast shield 300 having a flexible funnel 310, 320, 330 and a support structure 340 can comprise a sealing section 321 at the second end 320 of the flexible funnel. The sealing section 321 extends over a second end 342 of the support structure 340 and allows a sealing of the breast shield 300 when it is placed into the port 530 of the expression kit 501.

FIG. 12 discloses an alternative aspect of the sealing of the funnel against a port of the expression kit. In the aspect according to FIG. 12, a sealing section 321 is not provided at the end of the second end 320 but the sealing section 321 may extend through holes 342*a* in the second end 342 of the support structure. When the breast shield is then introduced into the port 530 of the expression kit 501, the sealing section 321 can seal the breast shield arrangement against the port 530.

Figure 13A:
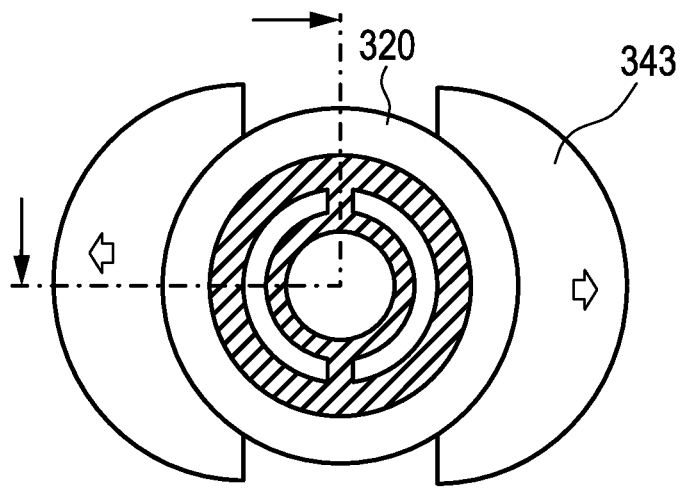
FIGS. 13A and 13B each show a schematic cross section of a breast shield arrangement according to an aspect of the invention.
Figure 13B:
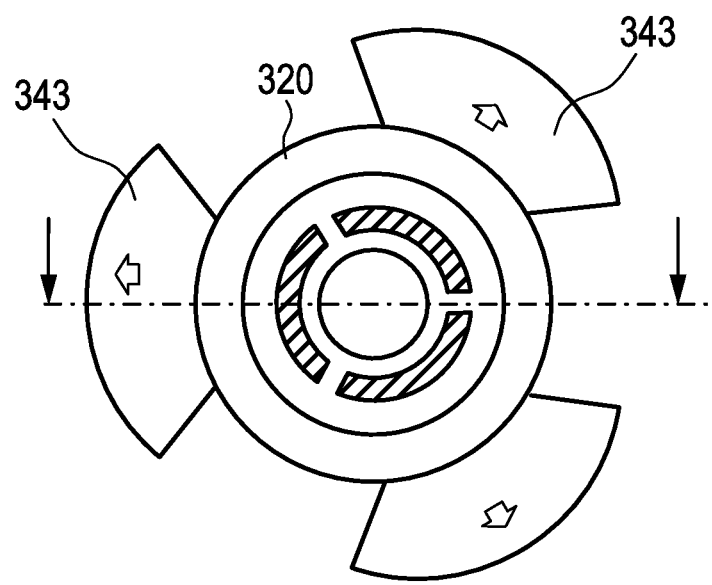

FIGS. 13A and 13B each show a schematic cross section of a breast shield arrangement according to an aspect of the invention. In FIGS. 3A and 3B, a cross section of a breast shield arrangement is depicted with the intermediate portion 330 and two or three legs 343.

According to an aspect of the invention, a breast shield arrangement 300 for a breast pump is provided, comprising a first end as a first sealing portion 310 adapted to seal the breast shield arrangement 300 against a breast 200 of a user, a second end 320 adapted to be coupled to an expression kit 500, and a flexible collapsible intermediate portion 330 between the first and second end 310, 320 of the breast shield arrangement 300, said intermediate portion 330 having a circumferentially extending wall defining a first volume V1 which is adapted to receive a nipple 210 and at least part of an areola 220 of the breast 200 of a user, said intermediate portion 330 having a first end 331, a curved portion 332 and a second end 333, wherein the curved portion 332 comprises a second sealing portion 332*c*, said second sealing portion 332*c* being adapted to seal the curved portion 332 against the nipple 210 and at least part of the areola 220 of the breast 200 of a user when a vacuum is applied at the second end 320 of the breast shield arrangement 300, wherein an inner diameter of the intermediate portion 330 is continuously reduced between a first to the second end of the curved portion 332, wherein a support structure 240 is provided to support the intermediate portion 330, wherein the support structure 340 and the intermediate portion 330 are made by 2K injection molding.

According to a further aspect of the invention, a breast shield arrangement 300 for a breast pump is provided which furthermore comprises a first end as sealing portion 310 adapted to seal the breast shield arrangement 300 against a breast 200 of a user, a second end 320, and an intermediate portion 330 between the first and second end 310, 320 of the breast shield arrangement 300 being adapted to receive a nipple 210 and at least part of an areola 220 of the breast 200 of a user, said intermediate portion 330 having a first end 331, a curved portion 332 and a second end 333, wherein a length of the curved portion 332 is greater than a distance between the first and second end 331, 333 of the intermediate portion 330, wherein the curved portion 332 has at least a concave shape near the first end 331 of the intermediate portion 330, wherein an inner diameter of the intermediate portion 330 is continuously reduced between a first to the second end of the curved portion 332.

According to a further aspect of the invention, the curved portion 332 has at least a concave shape near the first end 331 of the intermediate portion 330 and a convex shape near the second end 333 of the intermediate portion 330.

According to an aspect of the invention, the curved portion 332 comprises a first and second end 332a, 332d and a first and second curved section 332b, 332c, wherein the first curved section 332b is of a concave shape; wherein the second curved section 332c is of a convex shape; wherein the first and second end 332a, 332d of the curved portion 332 corresponds to the first and second end 331, 333 of the intermediate portion 330, respectively, wherein the first and/or second curved section 332b, 332c correspond to a first contact point being a first point of contact with a nipple 210 of a user when a vacuum is applied to the breast shield arrangement 300 and the intermediate portion collapses.

Other variations of the disclosed embodiment can be understood and effected by those skilled in the art in practicing the claimed invention from a study of the drawings, the disclosure and the appended claims.

In the claims, the word "comprising" does not exclude other elements or steps and in the indefinite article "a" or "an" does not exclude a plurality.

A single unit or device may fulfil the functions of several items recited in the claims. The mere fact that certain measures are recited in mutual different dependent claims does not indicate that a combination of these measurements cannot be used to advantage. A computer program may be stored/distributed on a suitable medium such as an optical storage medium or a solid state medium, supplied together with or as a part of other hardware, but may also be distributed in other forms such as via the internet or other wired or wireless telecommunication systems.

Any reference signs in the claims should not be construed as limiting the scope.

The invention claimed is:

1. A breast shield arrangement for a breast pump, comprising:
   a breast receiving portion having a flexible collapsible funnel and a rigid frame which are made as a single unit by a two component manufacturing,
   said flexible funnel having a circumferentially extending wall,
   said breast receiving portion having a first and second end,
   wherein the flexible funnel and the rigid frame are connected at the first and second end of the breast receiving portion at least at first and second positions during the two component manufacturing;
   wherein the flexible funnel is configured to collapse when a vacuum is applied only to the breast receiving portion via the second end of the breast receiving portion,
   wherein the flexible funnel comprises an at least partially circumferentially extending concave portion as seen from the first end of the breast receiving portion,
   wherein the concave portion is coupled to the first end of the breast receiving portion, and
   wherein the vacuum applied at the second end of the breast receiving portion is the only vacuum in the breast shield arrangement.

2. The breast shield arrangement for a breast pump according to claim 1, wherein the flexible funnel further comprises a convex portion which forms in the collapsed state of the funnel a sealing portion configured to seal a part of the nipple and/or the areola against a vacuum in the breast receiving portion.

3. The breast shield arrangement for a breast pump according to claim 1, wherein the flexible funnel has in a collapsed state at least two lobes.

4. The breast shield arrangement for a breast pump according to claim 1, wherein the rigid frame comprises a first and second end as well as at least one leg between the first and second end, and wherein the flexible funnel and at least one leg are at least partly connected at at least one third position during the two component manufacturing.

5. The breast shield arrangement for a breast pump according to claim 4, wherein the concave portion of the flexible funnel is coupled at the third position to the at least one leg.

6. The breast shield arrangement for a breast pump according to claim 1, wherein the two component manufacturing comprises a two component injection molding, a three component 3K injection molding, a 3D printing or rapid prototyping.

7. The breast shield arrangement for a breast pump according to claim 1, wherein
   when no vacuum is applied to the breast shield arrangement via the second end, the flexible funnel is configured such that a nipple of a user can be inserted without coming into contact with the concave portion.

8. A breast pump comprising:
   a breast shield arrangement according to claim 1, and
   an expression kit having a first port,
   wherein the first port is configured to receive the second end of the breast receiving portion,
   wherein the flexible funnel comprises a third circumferential sealing portion at the second end, said third sealing portion being configured to seal the breast receiving portion against the expression kit.

9. A breast shield arrangement for a breast pump, comprising:
   a breast receiving portion having a flexible collapsible funnel and a rigid frame which are made as a single unit by two component manufacturing,
   said flexible funnel having a circumferentially extending wall,
   said breast receiving portion having a first and second end,
   wherein the flexible funnel and the rigid frame are connected at the first and second end of the breast receiving portion at at least a first and second position during the two component manufacturing;

wherein the flexible funnel is configured to collapse when a vacuum is applied only to the breast receiving portion via the second end of the breast receiving portion, wherein the rigid frame comprises a first and second end as well as at least one leg between the first and second end, wherein the flexible funnel and at least one leg are at least partly connected during the manufacturing at at least a third position, and wherein the vacuum applied at the second end of the breast receiving portion is the only vacuum in the breast shield arrangement.

10. The breast shield arrangement for a breast pump according to claim 9, wherein the first end of the flexible funnel and the first end of the rigid frame form a first sealing portion which is configured to receive and seal the breast shield arrangement against a breast of a user.

11. The breast shield arrangement for a breast pump according to claim 9, wherein the flexible funnel comprises an at least partially circumferentially extending concave portion as seen from the first end of the breast receiving portion, and wherein the concave portion is coupled to the first end of the breast receiving portion.

12. The breast shield arrangement for a breast pump according to claim 11, wherein the flexible funnel comprises a convex portion between the concave portion and the second end of the breast receiving portion.

13. A breast pump comprising:
a breast shield arrangement according to claim 9 and an expression kit having a first port, wherein the first port is configured to receive the second end of the breast receiving portion, wherein the flexible funnel comprises a third circumferential sealing portion between the convex portion and the second end, said third sealing portion being configured to seal the breast receiving portion against the expression kit.

14. A method of operating a breast pump which comprises a breast shield arrangement and an expression kit, wherein the breast shield arrangement comprises a breast receiving portion having a flexible collapsible funnel and a rigid frame which are made as a single unit by two component manufacturing, wherein the flexible funnel has a circumferentially extending wall and the breast receiving portion has a first and second end, wherein the flexible funnel and the rigid frame are connected at the first and second end of the breast receiving portion at least at first and second positions during the two component manufacturing, wherein the flexible funnel comprises an at least partially circumferentially extending concave portion as seen from the first end of the breast receiving portion, wherein the concave portion is coupled to the first end of the breast receiving portion, the method comprising:

placing the flexible funnel over part of a breast including a nipple, and applying a vacuum at a second end of the breast receiving portion, wherein the vacuum applied only via the second end of the breast receiving portion is the only vacuum in the breast shield arrangement.

* * * * *